United States Patent [19]

Dhawan et al.

[11] Patent Number: 5,112,496

[45] Date of Patent: * May 12, 1992

[54] METHODS FOR INHIBITION OF SCALE IN HIGH BRINE ENVIRONMENTS

[75] Inventors: Balram Dhawan; Derek Redmore; John L. Przybylinski, all of St. Louis, Mo.

[73] Assignee: Petrolite Corporation, St. Louis, Mo.

[ * ] Notice: The portion of the term of this patent subsequent to Jun. 5, 2007 has been disclaimed.

[21] Appl. No.: 664,900

[22] Filed: Mar. 5, 1991

Related U.S. Application Data

[60] Continuation-in-part of Ser. No. 502,191, Mar. 30, 1990, abandoned, which is a division of Ser. No. 368,699, Jun. 15, 1989, Pat. No. 4,931,189, which is a division of Ser. No. 266,449, Nov. 2, 1988, abandoned.

[51] Int. Cl.⁵ .............................................. C02F 5/14
[52] U.S. Cl. .................... 210/700; 166/244.1; 252/180
[58] Field of Search ........................ 210/698–701; 252/180, 181; 166/244.1

[56] References Cited

U.S. PATENT DOCUMENTS

| | | | |
|---|---|---|---|
| 3,288,846 | 11/1966 | Irani et al. ............................ | 260/500 |
| 3,705,005 | 12/1972 | Cervi et al. ........................... | 21/2.7 |
| 3,809,654 | 5/1974 | Mitchell ............................... | 252/180 |
| 3,816,333 | 6/1974 | King et al. ........................... | 252/389 A |
| 4,008,574 | 5/1977 | Quinlan ................................ | 210/58 |
| 4,012,440 | 3/1977 | Quinlan ................................ | 260/502.5 |
| 4,051,110 | 9/1977 | Quinlan ................................ | 260/72 R |
| 4,075,243 | 2/1978 | Quinlan ................................ | 260/502.5 |
| 4,080,375 | 3/1978 | Quinlan ................................ | 210/700 |
| 4,187,245 | 2/1980 | Redmore et al. .................... | 260/502.5 |
| 4,234,511 | 11/1980 | Backman ............................. | 260/502.5 |
| 4,459,241 | 7/1984 | Wilson et al. ....................... | 260/502.5 |
| 4,857,205 | 8/1989 | Redmore et al. .................... | 210/700 |
| 4,931,189 | 6/1990 | Dhawan et al. ..................... | 210/700 |

FOREIGN PATENT DOCUMENTS 213865 9/1970 U.S.S.R. ............................ 260/502.5

*Primary Examiner*—Peter Hruskoci
*Attorney, Agent, or Firm*—Stanley M. Tarter; Kenneth Soloman

[57] ABSTRACT

A method for inhibiting oilfield scale formation including calcite in a high brine environment comprises introducing an effective amount of a scale inhibiting composition to a high brine environment susceptible to calcite scale formation. The environment has a total dissolved solids content of at least about 150 g/l, and the scale inhibiting composition comprises an aminomethylene posphonate of the formula

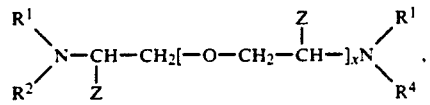

wherein x is 2 or 3, each Z is independently selected from among H and $CH_3$, and $R^1$, $R^2$, $R^3$, and $R^4$ are independently selected from among hydrogen and $-CH_2PO_3M_2$ wherein the M's are independently selected from among the hydrogen and cations associated with Lewis bases, such that at least about 80% of the $R^1$, $R^2$, $R^3$, and $R^4$ in the composition is $-CH_2PO_3M_2$.

2 Claims, No Drawings

METHODS FOR INHIBITION OF SCALE IN HIGH BRINE ENVIRONMENTS

CROSS REFERENCE TO RELATED APPLICATIONS

This application is a continuation-in-part application of prior application U.S. patent application Ser. No. 07/502,191, filed Mar. 30, 1990, now abandoned, which is a divisonal application of U.S. patent application Ser. No. 07/368,699, filed Jun. 15, 1989, U.S. Pat. No. 4,931,189, issued Jun. 5, 1990) which is a divisional application of U.S. patent application Ser. No. 07/266,449, filed Nov. 2, 1988 now abandoned.

BACKGROUND OF THE INVENTION

1. Field of the Invention

This invention relates to compositions and methods for inhibiting oil field scale formation, and more particularly to compositions and methods for inhibiting scale formation in high brine environments.

2. Prior Art

A common problem encountered in industrial activities and activities involving transport of water or transport of aqueous mixtures is the formation of scale on equipment, particularly on the inside surfaces of conduits. Oil field brines, and most commercial water contain a variety of alkaline earth metal cations, such as calcium, barium and strontium, as well as a variety anions such as bicarbonate, carbonate, sulfate, phosphate and silicate. When such ions are present in sufficient concentrations, they tend to combine to form precipitates. Scale, formed by the deposition of any of several types of such precipitates, including calcium carbonate, calcium sulfate and barium sulfate (barite), therefore tends to coat surfaces in contact with water. Buildup of such scale on, for example, the inside surfaces of conduits not only obstructs fluid flow, but also interferes with heat transfer across the surfaces, facilitates corrosion of the surfaces and harbors the growth of bacteria.

Conventionally, scale formation is inhibited by introducing a scale inhibiting composition to the aqueous environment. Various scale inhibiting compositions have been employed to inhibit scale formation, and several such compositions are illustrated in Redmore U.S. Pat. No. 4,187,245 et al., Backman U.S Pat. No. 4,234,511 and Quinlan U.S. Pat. Nos. 4,051,110 and 4,080,375. Scale inhibiting compositions, such as those disclosed in the above noted patents, have been found useful for inhibiting scale formation in many typical environments. However, they generally have limited solubility in high brine environments, that is, in brines having in excess of about 150 grams of total dissolved solids per liter of brine. Thus, conventional scale inhibitors generally have been found to be substantially less effective in high brine environments, such as those found in certain oil fields in the Rocky Mountains of the United States.

SUMMARY OF THE INVENTION

Briefly, therefore, the present invention is directed to a novel method for inhibiting scale information in a high brine environment. The method comprises introducing an effective amount of a scale inhibiting composition to a high brine environment susceptible to scale formation, said environment having at least about 150 g/l dissolved solids. The scale inhibiting composition comprises an aminomethylene phosphohonate of the formula

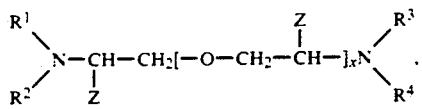

wherein x is an integral from 1 to 6, the Z's are independently selected from among hydrogen $-CH_3$, and $R^1$, $R^2$, $R^3$ and $R^4$ are independently selected from among hydrogen and $-CH_2PO_3M_2$ wherein the M's are independently selected from among hydrogen and cations associated with Lewis bases, such that at least 80% of the $R^1$, $R^2$, $R^3$ and $R^4$ in the composition is $-CH_2PO_3M_2$.

Among the several advantages found to be achieved by the present invention, therefore, may be noted the provision of a method for inhibiting scale formation in high brine environments and the provision of compositions useful in such methods.

DETAILED DESCRIPTION OF THE PREFERRED EMBODIMENTS

In accordance with this invention, certain novel aminomethylene phosphonates have been discovered which are useful for inhibiting scale information in a high brine environment. In particular, in contrast to conventional scale inhibitors, such compositions have been found to be soluble enough in high brines, and to maintain enough inhibitive activity in such brines, to be effective in inhibiting scale formation in high brines.

The aminomethylene phosphonates of this invention may be prepared by phosphonomethylation of an amine of the formula

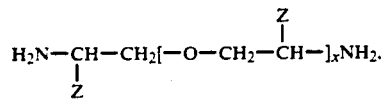

wherein x is an integer from 1 to 6 and the Z's are independently selected from among hydrogen $-CH_3$. It has been found that if x is to low, for example, 0, the resulting aminomethylene phosphate is not sufficiently soluble in the high brine environments to be sufficiently effective. On the other hand, if x is too high, such as 7 or higher, the aminomethylene phosphonate prepared from the amine does not adequately inhibit scale formation. In view of these constraints, it has been found that optimally, x should be 2 or 3. Preferably, both Z's are $-CH_3$.

The amine is added either in pure form or, if desired, as an aqueous solution, batchwise to a mixture of phosphorous acid and a second acid in a continuously stirred tank reactor, and the reaction mixture is heated to reflux, about 100° C. to about 120° C. However, because this addition step is exothermic, cooling may actually be necessary. For nearly complete phosphonomethylation, that is, phosphonomethylation in excess of about 80%, at least about 3.2 to about 4 moles of phosphorous acid per mole amine should be employed and enough of the second acid to maintain acidic conditions in the reaction mixture.

In order to maintain the acidity, the second acid should be a strong mineral acid, such as hydrochloric acid, and enough should be present in the mixture to neutralize the amine. Thus, if the second acid is hydrochloric acid, at least two moles of the hydrochloric acid per mole of amine should be employed, and preferably about three to about four moles of the hydrochloric acid per mole of amine should be employed. If water is present in the system, a greater proportion of the second acid should be used.

Formaldehyde (typically in a commercial solution such as formalin, a 37% by weight aqueous formaldehyde solution) in a molar amount at least about equal to the molar amount of the phosphorous acid, and preferably slightly greater, is added slowly to the reaction mixture. The temperature of the mixture is then maintained for about two to about four hours.

If the reaction mixture is refluxed at about 120° C., the system should be closed and heat added to maintain the temperature. Although such measures are not necessary if the reaction is conducted at 100° C., operation of the reaction at 100° C. results in greater formaldehyde residue and a lower reaction rate.

The amine therefore undergoes a nearly 100% conversion to aminomethylene phosphonate such that the product comprises aminomethylene phosphonate of the formula

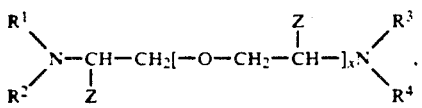

wherein x is an integer from 1 to 6 and the Z's are independently selected from among hydrogen and —CH$_3$, as determined by the amine precursor and R$^1$, R$^2$, R$^3$ and R$^4$ are independently selected from among hydrogen and —CH$_2$PO$_3$H$_2$. As a result of the nearly 100% conversion, at least about 80% of the R$^1$, R$^2$, R$^3$ and R$^4$ in the reaction product mixture of the aminomethylene phosphonate is —CH$_2$PO$_3$H$_2$. As discussed above, it is preferred that x be 2 or 3. It is also desired that as high a degree of phosphonomethylation as practical be achieved, and so it is preferred that at least about 90%, and optimally about 100% of the R$^1$, R$^2$, R$^3$ and R$^4$ in the reaction product mixture of the aminomethylene phosphonate is —CH$_2$PO$_3$H$_2$.

The reaction product may then be employed as a scale inhibitor. However, other additives as known in the art may be included to provide other benefits. For example, a freezing point depressant such as methanol, ethylene glycol or isopropanol may first be added to the product to avoid freezing of the inhibitor before contact with warm underground fluids. Typically, the scale inhibitor is diluted with water before use. The expanded solution thereby produced comprises from about 20% by weight to about 50% by weight of the aminomethylene phosphonate.

Alternatively, before use as a scale inhibitor, the reaction product may first be neutralized to some extent. Any Lewis base, such as an alkali metal hydroxide (e.g., NaOH or KOH), ammonium hydroxide, an amine or an oxyalkylated amine (e.g., ethanolamine), may be added to achieve the neutralization. Because the Lewis base is added merely to neutralize the product, a wide variety of bases is feasible, although, bases providing barium or calcium anions are undesirable in view of the proposed goal of scale inhibition.

Thus, if the reaction product is neutralized, the inhibitor would comprise a salt of the aminomethylated phosphonate wherein R$^1$, R$^2$, R$^3$ and R$^4$ are independently selected from hydrogen and —CH$_2$PO$_3$H$_2$ wherein each M is independently selected from among hydrogen (as a result of incomplete neutralization) and the cation associated with the Lewis base (for example, the sodium ion from sodium hydroxide). Accordingly, for example, M would be independently selected from among hydrogen, alkali metals, alkyl ammonium groups (especially of from about 1 to about 6 carbon atoms), hydroxyalkylammonium groups (especially of from about 1 to about 6 carbon atoms), and ammonium, depending on the whether neutralization has been carried out and on what Lewis base or bases have been employed for such neutralization. Thus, the salt analogs of the phosphonomethyl group —CH$_2$PO$_3$H$_2$ correspond to the formula —CH$_2$PO$_3$M$_2$. Most preferably, the M—s are sodium, potassium, ammonium or mono-, di- or triethanolamine radicals, or a mixture thereof.

As with the unneutralized inhibitor, a freezing point depressant, such as methanol, ethylene glycol or isopropanol may be added to the composition or treated composition, to avoid freezing of the composition and, typically, the scale inhibiting composition is diluted before use as a scale inhibitor. The expanded solution thereby produced comprises between about 20% by weight and about 30% by weight phosphonic acid or its salt.

In operation, for example in oil or gas fields, a scale inhibiting effective amount of the composition is in injected or otherwise delivered into the reservoir to provide a concentration of phosphonic acid or salt in the mixture in the conduit of between about 1 ppm and about 100 ppm to inhibit scale formation. It has been found that the phosphonic acid or salts of this invention are sufficiently soluble and effective in very high brines, such as many of the fields found in the Rocky Mountains, to provide a useful inhibitor in such environments.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

Jeffamine D-230 (a trade designation for an amine composition comprising a mixture of H$_2$NCH(CH$_3$)—CH$_2$[—O—CH$_2$—CH(CH$_3$)—]$_2$NH$_2$ and H$_2$NCH(CH$_3$)—CH$_2$[—O—CH$_2$—CH(CH$_3$)—]$_3$NH$_2$) (12.1 g) was added to a mixture of phosphorous acid (16.4 g), water (75 ml) and concentrated hydrochloric acid (75 ml) in a 500 ml 3-necked glass flask fitted with a reflux condenser, a magnetic stirrer, a thermometer and an additional funnel. The reaction mixture was heated to reflux (about 105° C.) and then 37% aqueous formaldehyde (16.2 g) was added dropwise over a thirty minute period. The reaction mixture was heated at reflux for an additional four hours after completion of the addition of formaldehyde. The reaction mixture was then cooled to 20° to 25° C. and stored as an acid mass. It was observed that about 95% of the NH groups were phosphonomethylated.

EXAMPLE 2

The solubility of several inhibitors was measured at three pH's in each of four types of water. A few standard commercial inhibitors and the following inhibitors were tested:

Inhibitor Structure

1. $R_2NCH(CH_3)CH_2[-OCH_2CH(CH_3)-]_xNR_2$
2. $R_2NCH(CH_3)CH_2[-OCH_2CH(CH_3)-]_yNR_2$ where R represents $-CH_2PO_3H_2$. Inhibitor 1 is a mixture of composition wherein x is 2 and of composition wherein x is 3. Inhibitor 2 is a mixture of composition wherein y is 5 and of composition wherein y is 6.

For each test, buffer solution (1 ml) and neutralized inhibitor (0.1 ml) were added to concentrated test water (9 ml). The buffer solution for pH 5.5 was 1.0M piperazine and 1.6M HCl, for pH 7.0 was 1.0M imidazole and 0.5M HCl, and for pH 8.5 was 1.0M "Tris" and 0.3M HCl. The concentrated test waters were fresh water, salt water, low calcium brine and high calcium brine (in which a precipitate, presumably gypsum, formed and was filtered off before use of the brine), and contained the following salts (per liter total concentrate):

| Salt | Fresh Water | Salt Water | Low Calcium Brine | High Calcium Brine |
|---|---|---|---|---|
| $MgCl_2 \cdot 6H_2O$ | 0.055 gm. | 4.68 gm. | 4.68 gm. | 24.34 gm. |
| $CaCl_2 \cdot 2H_2O$ | 0.148 gm. | 11.47 gm. | 11.47 gm. | 59.67 gm. |
| $SrCl_2 \cdot 6H_2O$ | 0.0027 gm. | 0.21 gm. | 0.21 gm. | 1.11 gm. |
| $BaCl_2$* | — | 0.273 ml | 0.273 ml | 2.73 ml |
| $Na_2SO_4$ | 0.083 gm. | 4.14 gm. | 4.14 gm. | 1.32 gm. |
| NaCl | 10.24 gm. | 33.26 gm. | 138.5 gm. | 169.6 gm. |

*3 × $10^{-3}$ M

The mixture was shaken and then held at room temperature for two hours. At the end of the two hours, the mixture was again shaken and an aliquot transferred to a 1 cm. cuvette. The transmittance for each test was measured with a spectrophotometer. Inhibitors 1, 2 and 4 were viscous concentrated products and so were diluted to 50% before testing. The results were as follows:

(% Transmittance, 1 cm cuvette, 1% solution)

| Inhibitor | pH | Fresh | Salty | Low Ca Brine | High Ca Brine |
|---|---|---|---|---|---|
| 1 | 5.5 | 100 | 100 | 100 | 100 |
|   | 7.0 | 100 | 100 | 100 | 100 |
|   | 8.5 | 99 | 98 | 98 | 98 |
| 2 | 5.5 | 100 | 100 | 100 | 98 |
|   | 7.0 | 100 | 100 | 99 | 99 |
|   | 8.5 | 99 | 99 | 96 | 78 |
| A* | 5.5 | 100 | 99 | 99 | 99 |
|   | 7.0 | 98 | 98 | 98 | 89 |
|   | 8.5 | 99 | 99 | 98 | 21 |
| B* | 5.5 | 100 | 97 | 98 | 94 |
|   | 7.0 | 98 | 98 | 95 | 35 |
|   | 8.5 | 97 | 97 | 95 | 10 |
| C* | 5.5 | 97 | 95 | 10 | 0 |
|   | 7.0 | 96 | 0 | 0 | 0 |
|   | 8.5 | 98 | 0 | 0 | 0 |
| D* | 5.5 | 99 | 0 | 2 | 7 |
|   | 7.0 | 99 | 2 | 10 | 4 |
|   | 8.5 | 98 | 3 | 1 | 2 |

*Commercial Inhibitor

Although the absolute numbers reported for solubility may not be very significant in that, for example, a transmittance value of 98% may or may not indicate slight haziness, 95% transmittance definitely indicates haziness and heavy cloudy precipitates resulted in a transmittance of less than 1%. Extremely insoluble inhibitors sometimes produced a phase separation between the inhibitor and water, resulting in transmittance levels as high as 10% due to the difficulty in achieving adequate dispersal between the phases. Inhibitors producing less that 20% transmittance should be considered insoluble.

EXAMPLE 3

Barite ($BaSO_4$) and gypsum ($CaSO_4 \cdot 2H_2O$) precipitation tests were conducted. First, buffer solution (100 μl) and an amount of inhibitor stock solution (usually 10 to 100 μl) were introduced to a culture tube. The buffer solutions were the same as those in Example 2. Then sulfate stock solution (5 ml) and a mixed alkaline earth chloride and sodium chloride solution (5 ml) were added to the tube. The tube was closed with a teflon lined plastic screw cap, shaken, and placed in a 40° C. water bath for about five minutes. After that, seed slurry (1 ml) was added to the tube and the tube was placed in a rocking basket in the bath to keep the seed suspended in solution and to ensure that the rate of precipitation was maximized and surface controlled rather than diffusion controlled. After about 30 minutes the sample was withdrawn and a "stopper" solution (100 μl) was added to halt precipitation. The tube was then shaken. In the case of the barite tests, the solution was filtered through a 0.45 micron syringe filter to remove seed crystals and the clear solution was sent in a labeled bottle for barium analysis. In the case of the gypsum test, the seed, which was much coarser than the barite seed, was allowed to settle to the bottom of the tube and an aliquot of the supernate was titrated for calcium with EDTA in a basic solution. An automated titrator using a calcium selectrode for end point determination was most convenient, although hand titration to a hydroxynaphthol blue end point gave identical results.

Stock solutions of the inhibitors to be tested were prepared initially at a concentration of 1 g/100 ml. Using 10 μl to 100 μl of the inhibitor solution gave test concentrations of 9 to 90 ppm of inhibitor. This stock solution was diluted 1/10 or 1/100 to cover lower concentration ranges. Actual amount used were picked from the $10^{0.1}$ series: 10, 12.6, 15.8, 20, 25, 32, 40, 50, 63, 79, 100 μl.

The following solutions were used in the gypsum tests:

| | |
|---|---|
| Sulfate Stock: | 27 g/l $Na_2SO_4$ (anhyd.) |
| Calcium I: | 28 g/l $CaCl_2 2H_2O$ |
| Calcium III: | 79 g/l $CaCl_2 2H_2O$, 220 g/L NaCl |
| Seed Slurry: | 10 g gypsum, 100 ml $H_2O$ |
| Stopper: | 2% SP-237 (a trade designation of Petrolite Corp.), 1.0 M trishydroxymethylaminomethane |

The following solutions were used in the barite tests:

| | |
|---|---|
| Sulfate Stock: | 0.33 g/l $Na_2SO_4$ (anhyd.) |
| Barium I: | 22 g/l NaCl*, 37.5 μl 1 M $BaCl_2$ |
| Barium III: | 283 g/l NaCl*, 474 μl 1 M $BaCl_2$ per liter |
| Seed Slurry: | 1 g barite, 250 ml $H_2O$ |
| Stopper: | 2% SP-245 (a trade designation of Petrolite |

-continued

| | |
|---|---|
| Corp.), 1.0 M trishydroxymethylaminomethane | |

*Reagent NaCl also contains 0.001% Ba which adds significantly to the total.

The gypsum conditions gave an initial saturation ratio of 5.0 (S.I.=0.7). Blanks attained a saturation ratio of 1.0 (S.I.=0.0). Percent protection is calculated based on the amount of calcium measured ($Ca_m$), the amount of calcium initially present ($Ca_i$) and the amount of calcium found for a blank run ($Ca_b$). Percent protection is calculated using the formula:

$$\% \text{ Protection} = \frac{Ca_m - Ca_b}{Ca_i - Ca_b} \times 100$$

The barite conditions gave an initial saturation ration of 10.0 (S.I.=1.0). The low TDS blanks attained a saturation ratio of 3.0 (S.I.=0.5) and the high TDS blanks attain a saturation ratio of 1.0 (S.I.=0.2). Percent protection is calculated in a manner analogous to that used for gypsum.

The spectrophotometric results were as follows:

PPM PHOSPHORUS REQUIRED FOR 50% PROTECTION AGAINST GYPSUM AT 40° C.

| | Gypsum Test Conditions | | | |
|---|---|---|---|---|
| | IC | | IIIC | |
| Inhibitor | pH 5.5 | pH 7.0 | pH 5.5 | pH 7.0 |
| 1 | 7 | 5.2 | 5.0 | 2.9 |
| 2 | 7 | 7 | 6.9 | 7 |
| HMDP4* | 2.1 | 2.1 | 2.1 | 2.1 |
| E** | 4.2 | 3.4 | 3.4 | 3.4 |
| A** | 6.9 | 6.3 | 3.5 | 2.9 |
| B** | 4.4 | 5.9 | 1.9 | 3.1 |

*Hexamethylenediaminetetramethylene phosphonic acid
**Commercial Inhibitor

PPM PHOSPHORUS REQUIRED TO MAINTAIN STATED BARIUM LEVEL IN SOLUTION AT 40° C. (80° C.)

| | Barite Test Conditions | | | |
|---|---|---|---|---|
| | IB (1.0 ppm $Ba^{2+}$) | | IIIB (18 ppm $Ba^{2+}$) | |
| Inhibitor | pH 5.5 | pH 7.0 | pH 5.5 | pH 7.0 |
| 1 | 27 | 2.0 | 0.44 (0.50) | 0.31 (0.17) |
| 2 | 23 | 14 | 0.69 (0.78) | 0.41 (0.20) |
| D* | 4 | 1.5 | 0.25 (0.10) | 0.16 (0.076) |

*Commercial Inhibitor

EXAMPLE 4

Calcite ($CaCO_3$) Precipitation Tests

As a general procedure, an amount of inhibitor stock solution (10 to 100 μl) was introduced to a new glass screw top culture tube. Then 5.00 ml of 0.050 molar sodium carbonate solution and 5.00 ml of a combined buffer and sodium chloride solution were added to the tube. Next 1.00 ml of a freshly prepared slurry of calcium carbonate seed crystals in 0.20 molar calcium chloride solution was added to the tube. The tube was closed with a polypropylene screw cap and placed in a basket on its side with the top angled higher than the bottom in a 40° C. thermostated water bath for five minutes in order to allow temperature and pressure to equilibrate. The tube was then rocked gently in the bath in order to suspend the seed material in solution and to ensure that the rate of precipitation was maximized and surface controlled rather than diffusion controlled.

After 60 minutes the tube was removed from the bath. The solution was immediately filtered through a 0.45 micron syringe filter to remove seed crystals, and a 0.500 ml aliquot of the filtrate diluted with 9.00 ml of deionized water in order to ensure that no further precipitation could occur. The amount of calcium relative to the maximum and minimum amounts that could occur under these test conditions were determined by DC Plasma Atomic Emission Spectrometry using matrix matched standards.

Stock solutions of the inhibitors to be tested were prepared at a concentration of 0.29 grams of organically bound phosphorus per liter of solution. This corresponds to between 1.1 and 1.8 grams of aminomethylenephosphonate per liter of solution depending on the identity of the compound under consideration. Using 10 μl of the inhibitor solution gave test concentrations of 0.26 mg/l to 2.6 mg/l of organically bound phosphorus or 0.97 mg/l to 16.3 mg/l of aminomethylenephosphonate. Actual amounts of inhibitor stock solutions used were picked from the $10^{0.1}$ series: 10, 12.6, 15.8, 20, 25, 32, 40, 50, 63, 79, 100.

The following solutions were used in the calcite tests:

| | |
|---|---|
| Buffer/Sodium Chloride: | 68 g/l imidazole. |
| | 57 g/l 36.5% HCl, |
| | 248 g/l NaCl |
| Seed Slurry in Calcium Chloride: | 2.50 ml 0.200 M $CaCl_2$ and |
| | 25 μl 0.1 M NaOH and |
| | 2.50 g calcite powder |

The total solids in the solution was 157 g/l and the pH was about 6.5.

Percent protection was calculated in a manner analogous to that used for gypsum in Example 3. The amount of inhibitor required to attain 50% protection calculated from a straight line fit to data points including both higher and lower percent protections.

The DC Plasma atomic emission spectrophotometer results were as follows:

| Inhibitor | mg/l of Organically Bound Phosphorus |
|---|---|
| 1 | 0.73 |
| 2 | 0.82 |
| DETP5* | 0.61 |

*Diethylenetriaminepentamethylenephosphonic acid, which is the active ingredient in commercial formulation D.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for inhibiting oilfield scale formation including calcite in a high brine environment comprising introducing an effective amount of a scale inhibiting composition to a high brine environment susceptible to calcite scale formation, said environment having a total dissolved solids content of at least about 150 g/l, and said scale inhibiting composition comprising an aminomethylene phosphonate of the formula

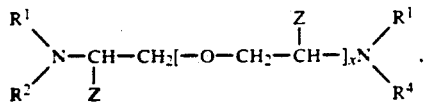

wherein x is 2 or 3, each Z is independently selected from the group consisting of H and CH$_3$, and R$^1$, R$^2$, R$^3$ and R$^4$ are independently selected from the group consisting of hydrogen and —CH$_2$PO$_3$M$_2$ wherein the M's are independently selected from the group consisting of hydrogen and cations associated with Lewis bases, such that at least about 80% of the R$^1$, R$^2$, R$^3$ and R$^4$ in the composition is —CH$_2$PO$_3$M$_2$.

2. A method as set forth in claim wherein each Z is —CH$_3$.

* * * * *